United States Patent [19]

Schaffner

[11] 4,212,639
[45] Jul. 15, 1980

[54] MEASURING APPARATUS FOR SETTING THE CORRECT PENETRATION DEPTH OF ROOT CANAL INSTRUMENTS

[75] Inventor: Alfred Schaffner, Breganzona, Switzerland

[73] Assignee: Polydent SA, Lugano, Switzerland

[21] Appl. No.: 958,096

[22] Filed: Nov. 6, 1978

[30] Foreign Application Priority Data

Nov. 17, 1977 [CH] Switzerland .................. 14217/77

[51] Int. Cl.² .................... A61G 1/14; A61C 5/02
[52] U.S. Cl. ...................................... 433/72; 433/102
[58] Field of Search .................. 32/60 R, 57; 433/72, 433/102

[56] References Cited

U.S. PATENT DOCUMENTS

| | | | |
|---|---|---|---|
| 3,938,253 | 2/1976 | Barnard | 32/40 R |
| 4,028,810 | 6/1977 | Vice | 32/57 |

*Primary Examiner*—Robert Peshock
*Attorney, Agent, or Firm*—Werner W. Kleeman

[57] ABSTRACT

A measuring device for setting the correct length or penetration depth of root canal instruments comprising relatively movable lower and upper portions and scale means cooperating with said two portions to enable accurately setting the intended depth of penetration of a root canal instrument used by the dentist. The upper portion has a substantially plate-like member having a top face whose distance from a top face or surface of the lower portion, defining a base portion, can be accurately set with the aid of the scale means. The root canal instrument then is inserted through a proper size hole in the plate-like member, onto the top face of which there has been previously placed a stopper, typically in the form of a disc, whereafter the root canal instrument is inserted through the stopper and the hole until the tip of the root canal instrument abuts against the top face or surface of the lower base portion. The stopper then engages about the shaft of the root canal instrument at the proper location from the tip of such instrument, corresponding to the intended working or penetration depth. At the plate-like member there is provided a substantially bowl-like depression or recess for receiving stoppers therein. The entire unit, namely the measuring device, the stoppers, and each calibrated root canal instrument can be conjointly sterilized.

6 Claims, 1 Drawing Figure

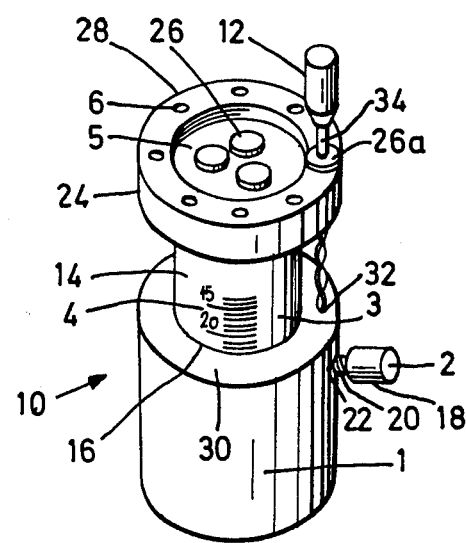

MEASURING APPARATUS FOR SETTING THE CORRECT PENETRATION DEPTH OF ROOT CANAL INSTRUMENTS

BACKGROUND OF THE INVENTION

The present invention relates to a new and improved construction of measuring device for accurately setting the correct length or depth of penetration of root canal instruments.

During dental work, particularly, for instance when a tooth is dead, it is necessary for the dentist to perform a root canal. Typically the dentist ascertains the depth through which the various size root canal instruments should penetrate into the root canal for removing the root from the tooth. To assist the dentist in his work there are known measuring devices wherein the root canal instruments are equipped with stoppers located at the proper point along each root canal instrument intended to be used, to ensure that the latter is inserted the proper depth into the root canal. These stoppers, which are typically formed of rubber or plastic, set the root canal instrument to the proper length or penetration depth for the root canal. This is normally determined by taking an X-ray of the tooth to be treated. During the root canal work different size root canal instruments are usually employed as the work progresses.

SUMMARY OF THE INVENTION

It is a primary object of the present invention to provide a measuring device of the character described which is structured such that the used stoppers can be stored and sterilized together with the measuring device.

A further significant object of the present invention aims at the provision of a new and improved construction of measuring device for adjusting the proper length of root canal instruments, wherein stoppers are used for setting the correct penetration depth of the various root canal instruments, and the measuring device is structured such that the used stoppers can be stored and sterilized together with the measuring device.

Now in order to implement these and still further objects of the invention, which will become more readily apparent as the description proceeds, the measuring device for setting the correct length of root canal instruments, as contemplated by the invention, comprises telescopically interfitting lower base portion and upper portion relatively movable with respect to one another. Scale means cooperate with these two portions to enable accurately setting the intended depth of penetration of the various root canal instruments used by the dentist. After setting the intended penetration depth the two telescopically interfitting portions can be positionally fixed by suitable arresting means. The upper portion has a top rim or plate-shaped member having a top face whose distance from the top face or surface of the lower base portion can be accurately set and fixed in position by the scale means and arresting means. Each root canal instrument then can be inserted through a proper size hole in the plate-shaped member or rim of the upper portion, over which there has been previously placed a stopper. Thereafter, the various size root canal instruments are each inserted through the related stopper and hole in the plate-shaped member until the tip of such root canal instrument abuts against the top face or surface of the lower base portion. The stopper then engages about the shaft of the related root canal instrument at the proper location from the tip of such instrument, corresponding to the intended working depth or depth of penetration for the instrument into the root canal. At the plate-shaped member or rim there is provided a bowl-like depression or recess for receiving the stoppers therein. The entire unit, namely the measuring device together with each such calibrated root canal instrument and the stoppers can be conjointly sterilized and the stoppers stored in the bowl-like depression until needed for use.

BRIEF DESCRIPTION OF THE DRAWING

The invention will be better understood and objects other than those set forth above, will become apparent when consideration is given to the following detailed description thereof. Such description makes reference to the annexed drawing wherein the single FIGURE schematically illustrates in perspective view a measuring device for setting the proper length or penetration depth of root canal instruments showing one of the instruments and a number of stoppers in the depression or recess of the upper portion.

DETAILED DESCRIPTION OF THE PREFERRED EMBODIMENTS

Describing now the drawing, in the single FIGURE there is shown in perspective view an exemplary embodiment of measuring device, generally indicated by reference character 10, for setting the correct length or penetration depth of root canal instruments, there being shown one such root canal instrument 12 which may be structured as a borer or reamer. This measuring device 10 will be seen to comprise the telescopically interfitting portions 1 and 3 constituting a substantially tubular-shaped lower base portion 1 and an upper portion 3 in the form of a plunger 14 which is movable within a central receiving bore 16 of the lower base portion 1. In order to fix the adjusted relative position between the displaceable upper portion 3 and the tubular-shaped lower portion 1 there are provided any suitable fixing means 2, such as a knurled arresting screw 18 which has its screw shaft 20 extending through a hole 22 of the lower base portion 1 and engaging the upper portion 3 to lock such in desired position. In the embodiment shown the upper portion 3 is of substantially cylindrical configuration and carries at outer surface of the cylindrical plunger 14 a scale means 4 bearing graduations between, by way of example, 13 mm to 37 mm.

The upper portion 3 includes an upper rim or plate-shaped member 24 at its upper end which is provided with at least one bowl-like depression or recess 5 at its upper surface. Spaced around the circumference of the plate-like member or rim 24 are a number of holes or bores 6 of different diameter through which there are inserted different size root canal instruments 12, only one such instrument being shown to simplify the illustration of the drawing. At the central bowl-like depression or recess 5 there are stored a number of stoppers 26, three such stoppers 26 being shown, which are used to fix the correct depth of penetration of each root canal instrument 12.

During use of the measuring device the dentist adjusts the cylindrical upper portion 3 in the correct position, such that the upper face 28 of the plate-like member 24 is at a desired spacing from the top face or surface 30 of the lower base portion 1 by an amount essentially corresponding to the intended depth of penetration of the root canal instruments 12. This adjusted position then is fixed by tightening the knurled arresting screw 18. Thereafter, over each hole or bore 6 through which there is intended to be inserted a root canal instrument 12, there is placed a stopper 26 and then the corresponding size root canal instrument 12 is inserted through the stopper and the related hole 6 of the plate-shaped member 24 until the free end 32 of the root canal instrument 12 abuts against the upper surface 30 of the lower base portion 1. As a result the stopper, such as the stopper 26a shown coacting with the root canal instrument 12, is properly positioned at the shaft or shank 34 of the root canal instrument 12, corresponding to the intended depth of penetration of such root canal instrument 12. In this way it is possible for the dentist to quickly and easily set the requisite penetration depth for different size root canal instruments 12 by means of the stoppers 26.

Due to the provision of the bowl-like depression or recess 5 it is possible to store the stoppers 26 together with the measuring device 10 and to sterilize the stoppers together with the measuring device 10 and the root canal instruments 12. This results in a considerable saving of time for the dentist when performing such type dental work. Also, the provision of the depression or recess 5 allows the stoppers 26 to be conveniently stored without any need to separately house the same or from becoming misplaced or lost, thereby again saving time for the dentist. The stoppers 26 are preferably formed in the form of small plates or discs of rubber or plastic, which prior to their initial use do not have any central hole. This is formed when the root canal instrument 12 is forced through the stopper, such as the shown stopper 26a, as it moves through the hole 6 of the upper rim or plate-shaped member 24 when setting the penetration depth of the related root canal instrument 12. The stoppers 26, after use, either can be thrown away, or, if desired, can be reused following sterilization. Prior to use, as mentioned, the stoppers as well as the root canal instruments should be sterilized. As equally mentioned, with the novel measuring device it is possible for there to be accomplished a conjoint sterilization of the measuring device 10, stoppers 26 and measuring instruments 12. The entire measuring device preferably is formed of a metal, such as eloxated aluminium, although it would be possible to use other materials, such as a suitable plastic which can be sterilized.

While there are shown and described present preferred embodiments of the invention, it is to be distinctly understood that the invention is not limited thereto, but may be otherwise variously embodied and practiced within the scope of the following claims. Accordingly,

What I claim is:

1. A measuring device for setting the correct depth of penetration of root canal instruments with stoppers, comprising:
   a lower base portion having a top face and a central bore;
   an upper portion received in the central bore of and telescopically movable with respect to the lower base portion, said upper portion including a plate member having an upper face, a plurality of holes arranged in said plate member in confronting relation with the top face of the lower base portion for receiving the root canal instruments;
   means for releasably fixing said upper and lower portions to one another such that the upper face of the plate member is located at a distance from the top face of the lower base portion;
   scale means provided on said upper portion for selectively setting the distance between said top face and upper face at a predetermined spacing corresponding to the intended depth of penetration of a root canal instrument;
   said plate member having recess means for receiving the stoppers used with the root canal instruments, whereby said stoppers can be stored in said recess means and sterilized together with the measuring device.

2. The measuring device as defined in claim 1, wherein:
   said lower base portion comprises a substantially tubular-shaped lower portion; and
   said upper portion comprises a substantially cylindrical upper portion telescopically interfitting in saidlower base portion.

3. The measuring device as defined in claim 1, wherein:
   said two portions are formed of metal.

4. The measuring device as defined in claim 3, wherein:
   said metal is eloxated aluminium.

5. The measuring device as defined in claim 1, wherein:
   said two portions are formed of plastic.

6. The measuring device as defined in claim 1, wherein:
   said recess means possesses a substantially bowl-like configuration.

* * * * *